United States Patent
Gliner et al.

(10) Patent No.: US 10,595,935 B2
(45) Date of Patent: Mar. 24, 2020

(54) SAFE ABLATION OF EUSTACHIAN TUBE EPITHELUM

(71) Applicant: Biosense Webster (Israel) Ltd., Yokneam (IL)

(72) Inventors: Vadim Gliner, Haifa (IL); Yaron Ephrath, Karkur (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 320 days.

(21) Appl. No.: 15/467,774

(22) Filed: Mar. 23, 2017

(65) Prior Publication Data
US 2018/0271580 A1    Sep. 27, 2018

(51) Int. Cl.
| | | |
|---|---|---|
| A61B 18/12 | (2006.01) | |
| A61B 18/14 | (2006.01) | |
| A61B 18/00 | (2006.01) | |
| A61B 34/20 | (2016.01) | |

(52) U.S. Cl.
CPC .. A61B 18/1485 (2013.01); *A61B 2018/0022* (2013.01); *A61B 2018/00327* (2013.01); *A61B 2018/00577* (2013.01); *A61B 2018/1467* (2013.01); *A61B 2034/2051* (2016.02); *A61B 2560/02* (2013.01)

(58) Field of Classification Search
None
See application file for complete search history.

(56) References Cited

U.S. PATENT DOCUMENTS

| | | | |
|---|---|---|---|
| 5,344,398 A | 9/1994 | Hara | |
| 6,425,853 B1 * | 7/2002 | Edwards | A61B 18/1477 600/29 |
| 2003/0208250 A1 | 11/2003 | Edwards et al. | |
| 2005/0240147 A1 * | 10/2005 | Makower | A61B 17/24 604/96.01 |
| 2008/0249553 A1 * | 10/2008 | Gruber | A61B 17/32002 606/171 |
| 2008/0255550 A1 | 10/2008 | Bell | |
| 2009/0093823 A1 * | 4/2009 | Chang | A61B 17/24 606/110 |
| 2009/0163890 A1 | 6/2009 | Clifford et al. | |
| 2010/0057074 A1 | 3/2010 | Roman et al. | |
| 2010/0198191 A1 | 8/2010 | Clifford et al. | |
| 2010/0274188 A1 | 10/2010 | Chang et al. | |
| 2012/0035437 A1 * | 2/2012 | Ferren | A61B 1/041 600/302 |
| 2012/0197245 A1 | 8/2012 | Burnett et al. | |
| 2013/0253387 A1 | 9/2013 | Bonutti et al. | |

FOREIGN PATENT DOCUMENTS

WO    WO 2014/012032 A2    1/2014

* cited by examiner

*Primary Examiner* — Linda C Dvorak
*Assistant Examiner* — Ryan T Clark
(74) *Attorney, Agent, or Firm* — Todd J. Burns

(57) ABSTRACT

Described embodiments include a method that includes inserting an ablation catheter into a Eustachian tube of a subject, and, using the ablation catheter, while the subject is awake, passing an ablating signal, which is audible to the subject, through epithelial cells that line the Eustachian tube, while controlling an amplitude of the ablating signal responsively to a loudness of the ablating signal as perceived by the subject. Other embodiments are also described.

10 Claims, 2 Drawing Sheets

SAFE ABLATION OF EUSTACHIAN TUBE EPITHELUM

FIELD OF THE INVENTION

The present invention relates to the field of medical procedures, and particularly to the treatment of blocked Eustachian tubes.

BACKGROUND

The Eustachian tube links the nasopharynx to the middle ear. In some cases, the epithelial cells that line the Eustachian tube may secrete an excess amount of fluid, causing the Eustachian tube to become blocked.

US Patent Application Publication 2013/0253387, whose disclosure is incorporated herein by reference, describes systems and methods for treating an occluded area in a body, accessing cavities or passages of the body, or reducing pathologic material in the body. Embodiments may be configured to apply vibratory energy to pathologic material in a treatment area of a body. A handle connected to an energy source may be configured to provide an energy signal. A transducer may be configured to receive the energy signal. An effector may be operatively coupled to the transducer. The effector may have a proximal end connected to the handle and a distal portion configured to apply vibratory energy to pathologic material. A cannula may have a longitudinal passage to receive at least a portion of the effector and/or be configured to expose at least the distal portion of the effector to the pathologic material or the treatment area.

US Patent Application Publication 2003/0208250, whose disclosure is incorporated herein by reference, describes a system for applying energy to one or more tissue structures proximate to the middle ear. The system includes means for locating and targeting a tissue structure to be treated, means for delivering energy to said targeted tissue, and means for monitoring treatment progress so that a treatment endpoint is determined and thermal damage to surrounding tissues minimized.

SUMMARY OF THE INVENTION

There is provided, in accordance with some embodiments of the present invention, a method that includes inserting an ablation catheter into a Eustachian tube of a subject, and, using the ablation catheter, while the subject is awake, passing an ablating signal, which is audible to the subject, through epithelial cells that line the Eustachian tube, while controlling an amplitude of the ablating signal responsively to a loudness of the ablating signal as perceived by the subject.

In some embodiments, the controlling of the amplitude is performed by another person responsively to feedback from the subject that indicates the loudness of the ablating signal as perceived by the subject.

In some embodiments, controlling the amplitude of the ablating signal includes increasing the amplitude of the ablating signal until the subject indicates that the subject is in pain from the loudness of the ablating signal.

In some embodiments, controlling the amplitude of the ablating signal further includes, subsequently, decreasing the amplitude of the ablating signal until the subject indicates that the subject is no longer in pain, and the method further includes, subsequently, passing the ablating signal at the decreased amplitude.

In some embodiments, the controlling of the amplitude is performed by the subject.

In some embodiments, controlling the amplitude of the ablating signal includes increasing the amplitude of the ablating signal until the subject is in pain from the loudness of the ablating signal.

In some embodiments, controlling the amplitude of the ablating signal further includes, subsequently, decreasing the amplitude of the ablating signal until the subject is no longer in pain, and the method further includes, subsequently, passing the ablating signal at the decreased amplitude.

In some embodiments, the ablating signal has a frequency of between 0.1 and 10 kHz.

In some embodiments, the ablating signal has a modulating frequency of between 0.1 and 10 kHz.

In some embodiments, the catheter includes a balloon and a plurality of electrodes coupled to the balloon, and passing the ablating signal includes passing the ablating signal between the electrodes.

The present invention will be more fully understood from the following detailed description of embodiments thereof, taken together with the drawings, in which:

DETAILED DESCRIPTION OF EMBODIMENTS

Overview

In embodiments of the present invention, an ablation catheter is used to ablate epithelial cells that line a Eustachian tube, in order to reduce the amount of fluid that is secreted into the tube. To help prevent damage to any sensitive tissue or organs, such as the cochlea or auditory nerve, that are near the Eustachian tube, the ablating signal is applied at audio frequencies (e.g., frequencies between 0.1 and 10 kHz), with the subject fully awake, such that the subject can indicate if the amplitude of the signal is too high.

Typically, to increase the efficacy of the procedure and/or reduce the duration of the procedure, the ablation is performed with the ablating signal having the maximum amplitude that can be achieved without causing pain to the subject. This amplitude may be referred to as the "maximum safe" amplitude, since it is assumed that as long as the subject is not in pain, there is little risk of any collateral damage occurring. To find the maximum safe amplitude, the amplitude of the ablating signal is increased from its initial value until the subject indicates that the signal is too loud, and the amplitude is then reduced to slightly below the pain threshold of the subject.

In general, in the field of ablation procedures, audio-frequency ablation is less common than radiofrequency (RF) ablation, since safety standards require that lower frequencies be transmitted into the body with less power, relative to higher frequencies. Advantageously, however, the present inventors have realized that ablation within the Eustachian tube requires relatively little power, such that audio frequencies may be effectively applied even if the amplitude (and hence power) of the ablating signal is limited by the pain threshold of the subject.

Method Description

Figure 1:
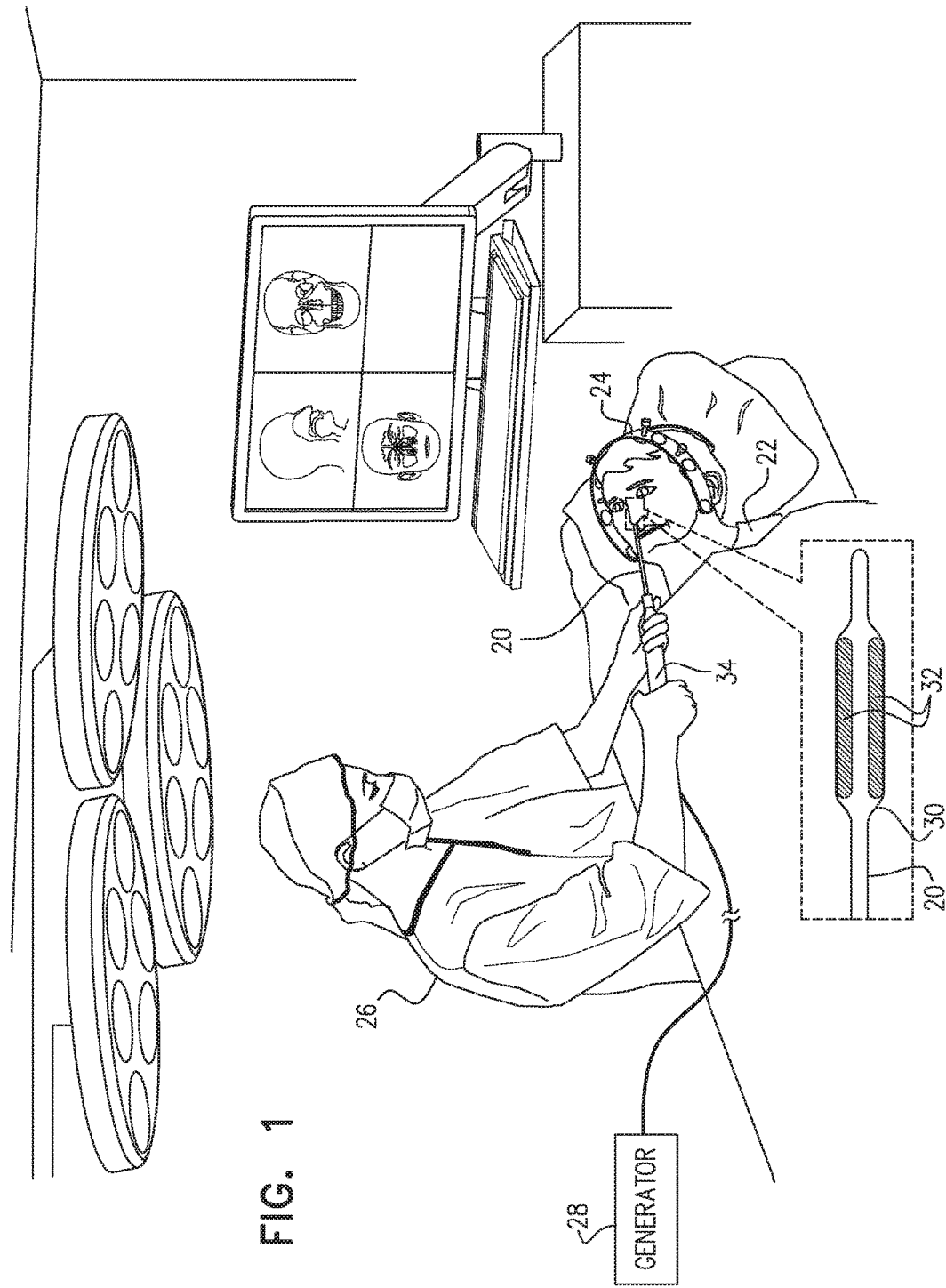
FIG. 1 is a schematic illustration of a method for treating a Eustachian tube of a subject, in accordance with some embodiments of the present invention.

Reference is initially made to FIG. 1, which is a schematic illustration of a method for treating a Eustachian tube of a subject 22, in accordance with some embodiments of the present invention.

FIG. 1 depicts a physician 26 inserting an ablation catheter 20 into the Eustachian tube of subject 22. As shown, catheter 20 may be inserted through a nostril of the subject; alternatively, the catheter may be inserted through a hole in an eardrum of the subject. Subsequently to the insertion of the catheter, the catheter is navigated to the Eustachian tube (e.g., using a handle 34 of the catheter), and is then used to ablate epithelial cells that line the tube. Subject 22 remains awake at least while the ablating signal is applied.

In some embodiments, a magnetic tracking system is used to navigate the catheter to the Eustachian tube. For example, the subject may wear a headband 24, comprising a plurality of magnetic generators that generate a magnetic field, and the distal end of the catheter may comprise an electromagnetic sensor (not shown). In response to the magnetic field sensed by the sensor, a processor may ascertain the position and orientation of the distal end of the catheter. Alternatively, the catheter may be navigated under fluoroscopy, and/or under endoscopy.

Typically, the distal end of catheter 20 comprises a balloon 30, to which are coupled a plurality of electrodes 32. Typically, balloon 30 is inflated after the distal end of the catheter is inserted into the Eustachian tube. Following the inflation of the balloon, an ablating signal, supplied by a generator 28, is passed between electrodes 32, such that the ablating signal passes through the epithelial cells that line the Eustachian tube.

It is noted that any suitable number of electrodes 32 may be coupled to balloon 30, in any suitable configuration. Electrodes 32 may be shaped as strips, as shown in FIG. 1, or may have any other suitable shape. It is further noted that the ablation catheter 20 need not necessarily comprise a balloon; rather, the scope of the present disclosure includes the use of any suitable type of ablation catheter configured to pass ablating signals into tissue.

In some embodiments, the ablating signal generated by generator 28 has an audio frequency, i.e., a frequency that is audible to the human ear, such as any frequency between 0.1 and 10 kHz. In other embodiments, the ablating signal has a higher frequency, such as a radio frequency, but is modulated by a modulating signal having an audio frequency. In either case, the ablating signal is audible to subject 22, such that the subject may provide feedback, indicating the loudness of the signal as perceived by the subject, to physician 26. In response to this feedback, the physician may control the amplitude of the ablating signal.

Figure 2:
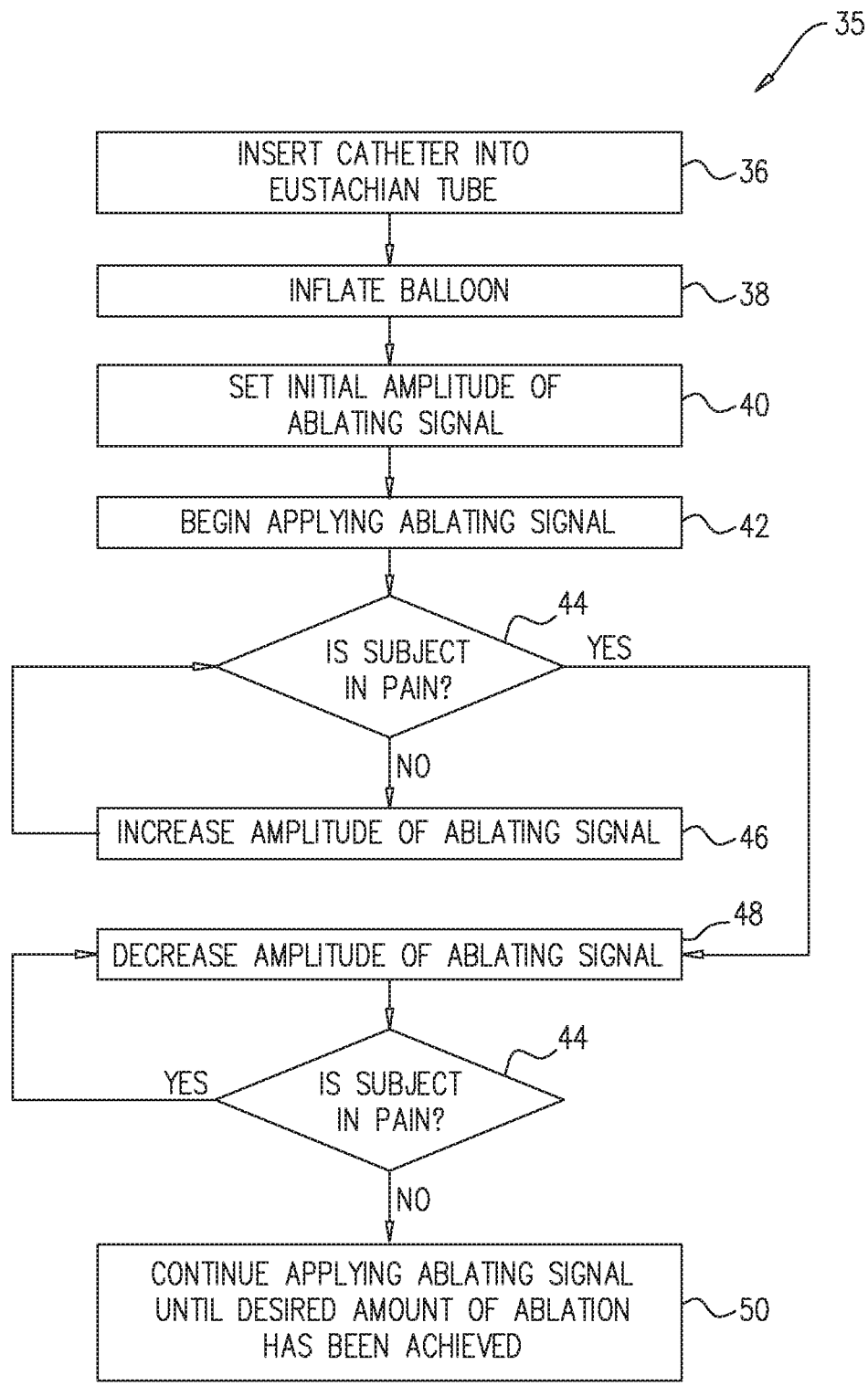
FIG. 2 is a flow diagram for a method for treating a Eustachian tube of a subject, in accordance with some embodiments of the present invention.

Reference is now made to FIG. 2, which is a flow diagram for a method 35 for treating a Eustachian tube of a subject, in accordance with some embodiments of the present invention.

Method 35 begins with an inserting step 36, at which catheter 20 is inserted into the subject's Eustachian tube, followed by an inflating step 38, at which balloon 30 is inflated, as described above with reference to FIG. 1. Subsequently, at a setting step 40, the physician sets the initial amplitude of the ablating signal. Typically, this initial amplitude is relatively low.

Subsequently, at a beginning step 42, the physician begins applying the ablating signal to the epithelium lining the subject's Eustachian tube, by passing the ablating signal between electrodes 32 on balloon 30. The physician then repeatedly increases the amplitude of the ablating signal at an increasing step 46, while checking, at a checking step 44, whether the subject is in pain from the ablating signal. For example, after each increase in amplitude, the physician may ask the subject if the signal is too loud. Alternatively or additionally, the physician may listen for any indication of pain from the subject, without explicitly asking the subject for feedback. As long as the subject does not indicate that the signal is too loud, the physician continues to increase the signal amplitude at increasing step 46.

Upon the subject indicating that the subject is in pain from the loudness of the ablating signal, the physician stops increasing the amplitude of the ablating signal, and instead, at a decreasing step 48, decreases the amplitude of the ablating signal. The physician may then continue to decrease the amplitude, if the subject continues to indicate that he is in pain. Typically, however, since the amplitude is increased only in small increments, it is not necessary to decrease the amplitude by more than a small amount, since a small decrease will move the amplitude of the signal below the pain threshold of the subject.

Upon the subject indicating the subject is no longer in pain, the physician stops decreasing the amplitude of the ablating signal. Subsequently, at an ablating step 50, the physician continues applying the ablating signal at the decreased amplitude, typically without any further changes to the amplitude (unless, for example, such changes are requested by the subject), until the desired amount of ablation has been achieved.

In some embodiments, the subject himself, rather than the physician or another person, controls the amplitude of the ablating signal responsively to the loudness of the ablating signal as perceived by the subject. For example, responsively to the perceived loudness of the signal, the subject may control the amplitude using a control device that is wiredly or wirelessly connected to the generator (or to a processor that controls the generator). In such embodiments, the subject may identify the maximum safe amplitude by increasing the amplitude until he is in pain, and subsequently decreasing the amplitude until he is no longer in pain. Subsequently, the ablating signal may be passed at the maximum safe amplitude, as described above.

In some embodiments, alternatively or additionally to applying an electrical ablating signal as described above, hot water is cycled through balloon 30, such as to ablate the epithelium in the Eustachian tube by the application of heat.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
inserting an ablation catheter into a Eustachian tube of a subject; and
using the ablation catheter, while the subject is awake, passing an ablating signal, which is audible to the subject, through epithelial cells that line the Eustachian tube, while controlling an amplitude of the ablating signal responsively to a loudness of the ablating signal as perceived by the subject.

2. The method according to claim 1, wherein the controlling of the amplitude is performed by another person responsively to feedback from the subject that indicates the loudness of the ablating signal as perceived by the subject.

3. The method according to claim 2, wherein controlling the amplitude of the ablating signal comprises increasing the amplitude of the ablating signal until the subject indicates that the subject is in pain from the loudness of the ablating signal.

4. The method according to claim 3, wherein controlling the amplitude of the ablating signal further comprises, subsequently, decreasing the amplitude of the ablating signal until the subject indicates that the subject is no longer in pain, and wherein the method further comprises, subsequently, passing the ablating signal at the decreased amplitude.

5. The method according to claim 1, wherein the controlling of the amplitude is performed by the subject.

6. The method according to claim 5, wherein controlling the amplitude of the ablating signal comprises increasing the amplitude of the ablating signal until the subject is in pain from the loudness of the ablating signal.

7. The method according to claim 6, wherein controlling the amplitude of the ablating signal further comprises, subsequently, decreasing the amplitude of the ablating signal until the subject is no longer in pain, and wherein the method further comprises, subsequently, passing the ablating signal at the decreased amplitude.

8. The method according to claim 1, wherein the ablating signal has a frequency of between 0.1 and 10 kHz.

9. The method according to claim 1, wherein the ablating signal has a modulating frequency of between 0.1 and 10 kHz.

10. The method according to claim 1, wherein the catheter includes a balloon and a plurality of electrodes coupled to the balloon, and wherein passing the ablating signal comprises passing the ablating signal between the electrodes.

* * * * *